US010295472B2

(12) United States Patent
Xie et al.

(10) Patent No.: US 10,295,472 B2
(45) Date of Patent: May 21, 2019

(54) ASSAY READER OPERABLE TO SCAN A TEST STRIP

(75) Inventors: Tong Xie, San Jose, CA (US); Benny Wing Hung Lai, Fremont, CA (US)

(73) Assignee: Alverix, Inc., Franklin Lakes, NJ (US)

( * ) Notice: Subject to any disclaimer, the term of this patent is extended or adjusted under 35 U.S.C. 154(b) by 292 days.

(21) Appl. No.: 12/774,138

(22) Filed: May 5, 2010

(65) Prior Publication Data

US 2011/0275162 A1 Nov. 10, 2011

(51) Int. Cl.
| | | |
|---|---|---|
| *G01N 21/01* | (2006.01) | |
| *G01N 33/00* | (2006.01) | |
| *G01N 21/78* | (2006.01) | |
| *G01N 21/84* | (2006.01) | |

(52) U.S. Cl.
CPC ......... *G01N 21/78* (2013.01); *G01N 21/8483* (2013.01)

(58) Field of Classification Search
CPC .............. G01N 21/8483; G01N 21/01; G01N 15/0205; G01N 2035/00108; G01N 21/84; G01N 2201/126; G01N 25/4813; G01N 25/4873; G01N 31/22; G01N 2021/177; G01N 2021/593; G01N 2021/8488; G01N 2035/00118
See application file for complete search history.

(56) References Cited

U.S. PATENT DOCUMENTS

| | | |
|---|---|---|
| 3,905,767 A | 9/1975 | Morris et al. |
| 4,197,088 A | 4/1980 | Meserol et al. |
| 4,267,261 A | 5/1981 | Hallman et al. |
| 4,275,149 A | 6/1981 | Litman et al. |
| 4,299,916 A | 11/1981 | Litman et al. |
| 4,366,241 A | 12/1982 | Tom et al. |
| 4,400,353 A | 8/1983 | Meserol et al. |
| 4,647,544 A | 3/1987 | Nicoli et al. |
| 4,666,309 A | 5/1987 | Barry et al. |
| 4,806,311 A | 2/1989 | Greenquist |

(Continued)

FOREIGN PATENT DOCUMENTS

| | | |
|---|---|---|
| EP | 0291194 | 11/1988 |
| EP | 0653625 | 5/1995 |
| EP | 2 270 495 | 1/2011 |

OTHER PUBLICATIONS

Extended European search report for European Application No. 11 164 721.0, dated Aug. 10, 2011.

*Primary Examiner* — Christopher Adam Hixson
(74) *Attorney, Agent, or Firm* — Knobbe Martens Olson & Bear LLP

(57) ABSTRACT

Low-cost assay test strip readers enable creation of profiles of analyte reactions detected on an assay test strip utilizing a simple detector fixedly mounted to a body of the reader. The detector may be a single detector, such as a photodetector, which detects an optical signal at a single point. The assay test strip is inserted and/or removed from the test strip reader and the detector detects the optical elements of the strip during such insertion and/or removal. The movement of the test strip with respect to the body enables the detector to scan a length of the test strip, thereby generating a profile of optical signals representing analyte reactions along a one-dimensional portion of the test strip. The reader may convert the detected profile into a displayable indication of analyte concentrations for diagnostic purposes.

28 Claims, 2 Drawing Sheets

(56) References Cited

U.S. PATENT DOCUMENTS

| | | | |
|---|---|---|---|
| 4,818,677 A | 4/1989 | Hay-Kaufman et al. | |
| 4,871,258 A * | 10/1989 | Herpichboehm et al. | 356/422 |
| 5,075,078 A | 12/1991 | Osikowicz et al. | |
| 5,094,955 A | 3/1992 | Calandra et al. | |
| 5,096,837 A | 3/1992 | Fan et al. | |
| 5,118,183 A | 6/1992 | Cargill et al. | |
| 5,118,428 A | 6/1992 | Sand et al. | |
| 5,118,630 A | 6/1992 | Glaze | |
| 5,132,097 A | 7/1992 | Van Deusen et al. | |
| 5,198,369 A | 3/1993 | Itoh et al. | |
| 5,221,616 A | 6/1993 | Kolb et al. | |
| 5,223,220 A | 6/1993 | Fan et al. | |
| 5,225,328 A | 7/1993 | Chang | |
| 5,252,459 A | 10/1993 | Tarcha et al. | |
| 5,415,994 A | 5/1995 | Imrich et al. | |
| 5,434,057 A | 7/1995 | Dorian | |
| 5,457,313 A | 10/1995 | Baylor et al. | |
| 5,500,375 A | 3/1996 | Lee-Own et al. | |
| 5,521,102 A | 5/1996 | Boehringer et al. | |
| RE35,306 E | 7/1996 | Chen et al. | |
| 5,536,646 A | 7/1996 | Sand et al. | |
| 5,541,069 A | 7/1996 | Mortensen et al. | |
| 5,591,645 A | 1/1997 | Rosenstein | |
| 5,598,007 A | 1/1997 | Bunce et al. | |
| 5,656,502 A | 8/1997 | MacKay et al. | |
| 5,658,801 A | 8/1997 | Poissant et al. | |
| 5,661,563 A | 8/1997 | Howard et al. | |
| 5,686,315 A | 11/1997 | Pronovost et al. | |
| 5,763,262 A | 6/1998 | Wong et al. | |
| 5,766,961 A | 6/1998 | Pawlak et al. | |
| 5,770,460 A | 6/1998 | Pawlak et al. | |
| 5,773,234 A | 6/1998 | Pronovost et al. | |
| 5,786,220 A | 7/1998 | Pronovost et al. | |
| 5,804,452 A | 7/1998 | Pronovost et al. | |
| 5,814,455 A | 9/1998 | Pronovost et al. | |
| 5,939,331 A | 8/1999 | Burd et al. | |
| 6,306,642 B1 | 10/2001 | Nelson et al. | |
| 6,352,862 B1 | 3/2002 | Davis et al. | |
| 2003/0068665 A1 * | 4/2003 | Kawamura et al. | 435/7.93 |
| 2005/0234368 A1 * | 10/2005 | Wong et al. | 600/583 |
| 2006/0197955 A1 * | 9/2006 | Koike | 356/446 |
| 2006/0240541 A1 | 10/2006 | Petruno et al. | |
| 2007/0188736 A1 * | 8/2007 | Fouquet et al. | 356/39 |
| 2008/0267823 A1 * | 10/2008 | Wang et al. | 422/68.1 |
| 2009/0155921 A1 * | 6/2009 | Lu | G01N 21/274 436/164 |

* cited by examiner

ASSAY READER OPERABLE TO SCAN A TEST STRIP

BACKGROUND

Assay test kits are currently available for testing a wide variety of medical and environmental conditions or compounds, such as for testing for the existence of a hormone, a metabolite, a toxin, or a pathogen-derived antigen. Most commonly these tests are used to enable medical diagnostics in the home testing context, the point of care testing context, or the laboratory context. For example, lateral flow tests rely on a form of immunoassay in which the test sample flows along a solid substrate via capillary action. Some tests are designed to make a quantitative determination, but in many circumstances the tests are designed to return or indicate a positive/negative qualitative indication. Examples of assays which enable such qualitative analysis include blood typing, most types of urinalysis, pregnancy tests, and AIDS tests. For these tests, with proper illumination, a visually observable indicator such as the presence of agglutination or a color change may indicate the result of the test.

Such assay-based tests can generally be divided into two categories. A first category includes assay-based tests in which, after the test sample flows along the solid substrate as noted above, the results of the tests (such as the colored or visible lines resulting from the test) are displayed or made visible to a human interpreter of the test. For example, a home pregnancy test may display one or more lines, wherein the perception by the human interpreter of a designated quantity of lines (such as two lines) indicates a positive outcome of the test (e.g., that the person taking the test is pregnant). Such tests can be inexpensive, but can also result in operator error or uncertainty by the human interpreter of the tests.

A second category of assay-based tests are tests which can be read by one or more opto-electronic assay readers. In such situations, a conventional assay strip-based test is read and/or analyzed by one or more opto-electronic devices. Such opto-electronic devices may utilize an optical detection technique to determine the concentration of particular analytes on the assay strip. These opto-electronic readers can vary in terms of the technology utilized to detect the results of the test. Generally, however, these opto-electronic devices are more expensive than their human-interpretable counterparts.

A first type of opto-electronic reader can include imaging-based opto-electronic readers. In such imaging-based readers, an array of detectors, such as a camera or other image detector, captures an image of a two-dimensional portion of the assay strip. For example, an image detector may include a CMOS or CCD image sensor which includes at least one semiconductor having a plurality of circuits that convert detected light to voltages. In such image sensors, circuitry on a silicon chip converts the voltages indicative of detected light into digital data representative of the sensed image. The device then applies known image processing algorithms to the captured image to accommodate certain imaging artifacts, such as mechanical tolerance artifacts or spatial non-uniformity artifacts. After the algorithms are applied, the circuitry analyzes the sensed image and outputs data indicative of a result. Such devices can also be modified to perform multiplexed tests, wherein a plurality of different portions of the assay strip are analyzed in the same test, and a result is determined based on each of the analyzed portions of the strip.

Known imaging-based readers suffer from certain drawbacks. Specifically, the cost associated with the optical detector and the supporting electronics required to analyze the image captured by the optical detector, such as a microcontroller with image processing capability, can be relatively high, and can prevent broad implementations of a consumer-based product utilizing such opto-electronic readers.

A second type of opto-electronic reader can include photodiode based opto-electronic readers. In such readers, one or more detectors of the reader is implemented as a photodiode, such as a PIN-diode, in which the amount of electricity flowing through the diode varies proportionately to the amount of optical signal detected, are used to collect data indicative of a representation of the results of the test as indicated visually by the assay strip. Corresponding circuitry implements one or more algorithms to analyze the amount of electricity flowing in the PIN-diode, and thus outputs or otherwise indicates the results of the assay test.

Photodiode-based readers also suffer from certain similar drawbacks to those discussed above with respect to imagers. While the circuitry required to drive known photodiode-based readers may be simpler than the circuitry required to drive similar imagers, and such readers may therefore be more cost effective than corresponding imagers, known photodiode-based readers suffer from drawbacks relating to their lack of scalability. Particularly, photodiode-based readers do not provide spatial information. For example, certain known PIN-based readers cannot differentiate between a plurality of visible lines on an assay strip. Other photodiode-based readers can differentiate between (and monitor) a plurality of different analyte regions on an assay strip only by including a plurality of immovable detectors in the form of a plurality of photodiode-diodes, with one detector corresponding to each potentially detected line. The cost and logistical issues associated with incorporating a plurality of photodiode-diodes in a single reader can thus be disadvantageous. Moreover, an existing reader with a plurality of detectors, implemented as a plurality of photodiode-diodes, may be limited to only analyzing assay test strips that detect the presence of certain types of analytes based on the static positions of the analyte regions, and thus based on the static positions of the detectors.

One known photodiode-based reader is implemented as the Clearblue® digital pregnancy test kit, manufactured and sold by SPD Swiss Precision Diagnostic. In this embodiment, two separate detectors (specifically, two separate PIN-diode based detectors) are positioned adjacent to a position associated with a control line and a test line, The qualitative result of the test (i.e., whether the provider of the sample for the test is pregnant), is based on which of these lines are visible following applying biological fluid to the assay test strip. Thus, while a plurality of lines of an assay test strip can be detected, the device is limited to tests which have analyte regions corresponding to the fixed positions of the photodiode detectors. Additional test lines require additional photodiode detectors, and thus are associated with additional costs and require development of different reader components.

To overcome the limitations of known photodiode-based readers attributable to the inability of such readers to simultaneously monitor a plurality of different portions of an assay test strip, certain known readers implement a single detector mounted on an electro-mechanical scanning mechanism. During testing, the scanning mechanism moves the photodiode of the reader across a stationary assay strip and provides a profile of an optical response representing analyte reactions along a one-dimensional portion of that assay strip. Most high-end commercial systems available today that utilize photodiode to monitor a plurality of different analytes contained in a single assay strip rely on such electro-mechanical scanning technology, wherein the scanner is driven by a stepper motor or other appropriate type of motor. However, such systems also suffer from certain drawbacks relating to the scanning apparatus' reliance on the stepper-motor. Such systems can be large, making portability difficult, and can be expensive, with costs ranging from two-thousand dollars to three-thousand dollars and upward.

Thus, it is desirable to create a portable, low-cost, stand-alone assay test strip reader which utilizes a single detector (or array of detectors) to detect the presence of a plurality of different analyte regions on the assay test strip without regard for the pattern of the analyte regions on the assay test strip.

SUMMARY

The present disclosure relates to an assay reader device that is capable of scanning for the presence of a plurality of lines at a plurality of analyte regions along the length of an assay test strip using at least one detector fixedly connected to a body of the assay reader, such that an assay test strip being examined moves relative to the at least one detector. By affixing one or more detectors to the body of the reader, and by thereafter relying on the relative motion between the assay test strip (such as during insertion and/or removal) and the body of the reader without an electro-mechanical scanning mechanism, the disclosed reader can utilize fixed detectors to scan a one- or two-dimensional portion of the assay test strip. Thus, the disclosed assay test reader does not rely on an electro-mechanical powered or motorized scanning mechanism, such as an expensive scanning mechanism driven by stepper motors or other robotics, to scan the assay test strip by moving the one or more detectors.

In various embodiments, the reader disclosed herein is discussed as including a sensor, such as a PIN-detector, which relies on a PIN-diode to determine the presence or absence of color on an assay test strip. It should be appreciated that this discussion of a sensor, implemented as a PIN-diode based detector, is provided as indicative of the features of an exemplary embodiment of the disclosed reader. That is, the disclosed reader is configured to utilize any appropriate type of detector to detect the presence or absence of a designated region on an assay test strip. For example, the disclosed reader may include any suitable type of detector capable of detecting the presence or absence of light, or other physically detectable properties including, magnetic field, polarization, wavelength, or radioactive emission. Such a detector could be a sensor such as a PIN-diode, a CCD sensor, a CMOS sensor, an InGaAs sensor, or any other suitable type of sensor. Further, the detector disclosed herein may rely on a single sensor element, such as a single PIN-diode, or may rely on an array of sensor elements, such as an array of PIN-diodes, to analyze the results of an assay test strip-based test. It should be appreciated that the discussion of specific embodiments of sensor herein does not limit the scope of the disclosed reader and is merely exemplary.

In one embodiment, the detector utilized by the disclosed reader generates a current proportional to the detected light and/or color on an assay test strip. For example, the detector may be a photodetector such as those described above, and may be configured to generate a current based on detected photons. In another embodiment, the disclosed detector generates current proportional to an amount of another characteristic of the disclosed assay test strip, wherein the characteristic can be an electromagnetic property, such as magnetic field, polarization, wavelength, or radioactive emission. For example, the disclosed detector may generate current proportional to an amount of a magnetic field generated in a designated region of an assay test strip. The detector utilized in the disclosed reader may detect the presence of other characteristics as appropriate depending on the type of assay test strip utilized and the mechanism by which the results of the test are determined.

The disclosed assay reader may additionally include control electronics to process the data resulting from scanning the test strip. For example, the control electronics may convert raw signal data generated during movement of the assay test strip with respect to the body of the assay reader into a profile of the assay test strip. The profile may indicate the presence or absence of certain analytes in a biological or chemical solution to which the assay test strip was exposed.

Further, in one embodiment the disclosed reader is discussed as being configured to receive an assay test strip and to determine one or more characteristics of that strip. It should be appreciated that as used herein, the term "assay test strip" or "assay strip" may refer to either an assay strip without any housing and/or casing, and/or may refer to an assay test strip which includes a portion on which the sample is disposed, contained within a housing or casing, such that the assay test trip is in fact an assembly or a cartridge in which the assay-based reactions occur. In one embodiment, wherein the assay test strip is not enclosed within a housing, the strip itself is inserted in the body of the reader, and the sensors disposed in the reader sense the presence or absence of appropriate characteristics of the strip itself. In another embodiment, wherein the assay test strip is disposed within a housing to form a cartridge, the assay test strip cartridge is inserted into the body of the disclosed reader, and the results of the test are determined by passing the detector(s) in the proximity of the reacting portion of the assay test strip. Thus, as they are used herein, the terms "assay test strip" and/or "assay strip" should not be limited in its interpretation to test strips without a housing. It should be understood that such terms can encompass cartridges in which an assay test strip substrate is enclosed within a housing, casing, or other enclosing element to form a cartridge which is inserted in the body of the disclosed reader.

In one embodiment, the disclosed reader also includes a display configured to output an indication of an outcome of a test. For example, the disclosed reader may include a display device configured to display data indicative of a qualitative outcome of a test, such as a "positive" or "negative" outcome determined by the control electronics connected to the at least one detector. The control electronics may determine this qualitative outcome based on the detected profile of the assay test strip, such that human error in interpreting visual characteristics of an assay test strip following exposure of the test strip to a biological or chemical fluid is reduced or eliminated. Alternatively or in addition, the disclosed reader may include at least one display configured to output a quantitative indication of a test. Moreover, the disclosed reader may include control electronics connected to the display, which determine an indication of one or more signal strengths determined by the detectors of the disclosed reader. In such an embodiment, the display device coupled to the detector via the control electronics may be configured to output an indication of a signal strength detected by the detector, which indication may represent the quantitative outcome of a test.

The present disclosure relates to assay test strip readers that include a body sized to receive an assay strip, the assay strip usable to perform an analyte test, at least one detector positioned within the body such that an inserting of the assay strip or a removing of the assay strip by an operator, which results in movement of the assay strip with respect to the body and the at least one detector, causes the at least one detector to detect a first signal based on a first point on the assay strip and to detect a second signal based on a different second point on the assay strip, and at least one signal converter electronically connected to the at least one detector, the at least one signal converter configured to receive the first signal and the second signal detected by the detector, generate at least one result signal indicative of a result of the analyte test based on the first optical signal and the second optical signal, and output the least one result signal.

In an embodiment, the body includes an assay strip receiving area sized to receive the assay strip.

In an embodiment, the first signal is a first optical signal indicative of an optical characteristic of the first point of the assay strip and wherein the second signal is a second optical signal indicative of the optical characteristic of the second point of the assay strip. In a further embodiment, the first optical signal is indicative of a measurement of color at the first point of the assay strip and wherein the second optical signal is indicative of a measurement of color at the second point of the assay strip.

In an embodiment, the assay test strip reader includes at least one audio/visual indicator affixed to the body and electronically connected to the at least one signal converter, the at least one audio/visual indicator configured to output an audio/visual representation of the at least one result signal. In a further embodiment, the analyte test is a medical diagnostic test, and wherein the audio/visual representation of the at least one result signal indicates a result of the medical diagnostic test. In an embodiment, the at least one result signal includes a visual display of a qualitative result of the medical diagnostic test.

In an embodiment, at least one result signal includes a visual display of a quantitative result of the medical diagnostic test based, at least on part, on a first intensity of the first signal based on the first point on the assay strip.

In an embodiment, the assay strip is slidably insertable in the body such that inserting the assay strip includes the operator sliding the assay strip in a first direction with respect to the body and removing the assay strip includes the operator sliding the assay strip in a different second direction with respect to the body.

In an embodiment, the at least one detector includes a photodiode detector. In another embodiment, the at least one detector includes an imager.

In an embodiment, the at least one result signal is indicative of an appearance of a one-dimensional portion of the assay strip.

In an embodiment, the at least one detector includes a plurality of detectors arranged as an array of detectors, and wherein the at least one result signal includes a two-dimensional representation of an appearance of the assay strip.

In an embodiment, a position sensing mechanism is included to detect at least one position of the assay test strip with respect to the reader. The position sensing mechanism can be based on an optical or an electro-mechanical mechanism. Examples of an electro-mechanical position sensing mechanism including a sliding or rotating potentiometer where the output signal is indicative of a relative position.

In an embodiment, the assay strip includes a test portion and an encoder portion, the test portion including at least one analyte reaction section, the encoder portion including a plurality of visible markings at a plurality of known positions, and wherein the at least one detector is positioned to detect an encoder optical signal indicative of the position of the assay strip within the body and to detect an analyte optical signal indicative of a reaction of at least one analyte.

In an embodiment, the at least one signal converter is configured to receive the encoder optical signal and to generate the at least one result signal based, at least in part, on the encoder optical signal.

In an embodiment, the encoder optical signal indicates a position of the at least one analyte reaction section on the assay strip and the at least one result signal is based on whether at least one line is displayed at the expected position of the at least one analyte reaction. In a further embodiment, the encoder optical signal including at least one characteristic of the analyte test is represented as a barcode.

In an embodiment, the assay test strip reader disclosed herein includes an assay test strip including a plurality of analyte reaction regions, a body, a spring mechanism including a release positioned within the body such that after the spring mechanism is loaded, activation of the release causes the spring mechanism to move the test strip outward relative to the body, at least one detector positioned within the body such that upon moving the assay test strip outward relative to the body, the detector detects an optical characteristic of each of the plurality of analyte reaction regions of the assay test strip, and at least one display device configured to output an indication of a profile of the assay test strip, the profile based on the plurality of optical characteristics associated with the plurality of analyte reaction regions of the assay test strip.

In an embodiment, the assay test strip is exposed to at least one biological fluid prior to moving the assay test strip relative to the body.

In an embodiment, the assay test strip is associated with a biological test, and which includes control electronics coupled to the at least one detector, the control electronics configured to generate the profile of the assay test strip, the profile indicative of a result of the biological test.

In an embodiment, the control electronics enable a connection to a separate processor-based device such that the profile of the assay test strip can be stored on a memory device of the separate processor-based device.

In an embodiment, the assay test strip reader includes at least one light source associated with the at least one detector, the at least one light source configured to illuminate at least one portion of the assay test strip being scanned with the at least one detector.

In an embodiment, the assay test strip is encased in an assay test strip housing, and wherein the body includes an assay test strip housing receiving portion sized to receive the assay test strip housing.

In an embodiment, an operator inserts the assay test strip in the body to load the spring mechanism, and wherein operator activates the release to move the test strip outward relative to the body.

In an embodiment, the at least one detector also detects the optical characteristic of each of the plurality of analyte reaction regions of the assay test strip prior to loading the spring mechanism.

In an embodiment, the assay test strip reader includes control electronics coupled to the at least one detector, and wherein the control electronics are configured to send a release signal to activate the release to cause the spring mechanism to move the test strip outward relative to the body, the release signal indicative that the at least one detector is ready to detect the optical characteristic of each of the plurality of analyte reaction regions of the assay test strip.

In an embodiment, insertion of the assay test trip causes the assay test strip reader to power on, or to wake up from a sleep state or a low-power state.

A method of analyzing an assay test strip disclosed herein includes enabling an operator to move the assay test strip relative to a body of an assay reader, the assay reader including at least one detector fixedly connected to the body, detecting a presence of at least one analyte reaction region based on at least one optical characteristic of the at least one analyte reaction region during the operator-caused moving of the assay test strip relative to the body of the assay reader, and outputting data indicative of the detected at least one optical characteristic of the at least one analyte reaction region using an audio/visual output device electrically connected to the at least one detector.

In an embodiment, the at least one detector includes a photodiode detector. In another embodiment, the at least one detector includes an imager.

In an embodiment, enabling the operator to move the assay test strip relative to the body of the assay reader includes enabling the operator to insert the assay test strip in the body of the assay reader, causing the assay test strip to engage at least one spring mechanism, and enabling the operator to cause the spring mechanism to release.

In an embodiment, outputting the data indicative of the detected at least one optical characteristic includes sending data to at least one processor-based device separate from the assay reader.

In an embodiment, the data is sent to the at least one processor-based device via a wired or wireless connection, such as a Bluetooth connection, a WiFi connection, or a USB connection.

In an embodiment, the disclosed method includes determining a profile of the assay test strip according to the detected presence of the at least one analyte reaction region.

In an embodiment, the at least one detector includes one assay detector fixedly connected to the body of the assay reader, and wherein the profile includes a profile of the optical response representing analyte reactions along a one-dimensional portion of the assay test strip.

In an embodiment, the at least one detector includes a plurality of assay detectors fixedly connected to the body of the assay reader in a linear arrangement perpendicular to a direction of motion of the assay test strip, and wherein the profile includes a two-dimensional profile of the assay test strip.

Additional features and advantages are described herein, and will be apparent from, the following Detailed Description.

DETAILED DESCRIPTION

The present disclosure relates to low-cost, portable assay test strip readers that are capable of detecting the presence of analytes in a biological sample using a plurality of spaced apart antibody regions on assay test strips. More particularly, the present disclosure relates to low-cost assay test strip readers that can determine the presence or absence of analyte reactions on assay test strips at a plurality of different locations on the assay test strips without requiring expensive scanning equipment and without requiring a separate detector to be aligned with each antibody region (and thus with each possible analyte reaction) of the test strip.

Conventional assay test strip readers are limited either because a different detector must be associated with each potential position of a visually identifiable analyte reaction, or because a scanning apparatus must use a complex, expensive, motor-driven scanner to scan a one- or two-dimensional portion of an assay test strip and to generate a one- or two-dimensional profile of that portion of the assay test strip. Such conventional assay test strip readers are too costly to be realistically implemented as robust home-use test kits.

The assay readers of the present disclosure represent improvements to known assay readers because they are low-cost and are able to detect the presence or absence of analyte reactions at a plurality of different locations on an assay test strip regardless of the number or positions of the potential reactions. The disclosed assay readers may enable these improved functionalities by utilizing one or more detectors or sensors which are each fixedly connected to a body, and by relying on the motion of an assay test strip (such as the insertion or removal of the assay test strip from the assay reader) with respect to both the body and the detector or sensor (which are fixed with respect to one another) to generate an analyte profile spanning a plurality of different regions or locations on the assay test strip.

Figure 1:
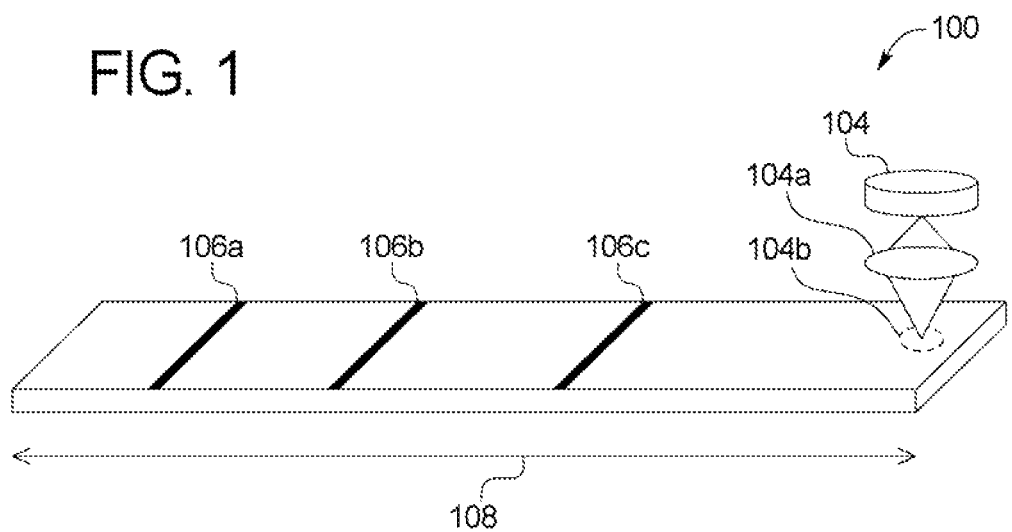
FIG. 1 illustrates a schematic diagram of an example assay reader containing three test lines as disclosed herein, including a single detector, without illustrating the body of the reader.
Figure 2:
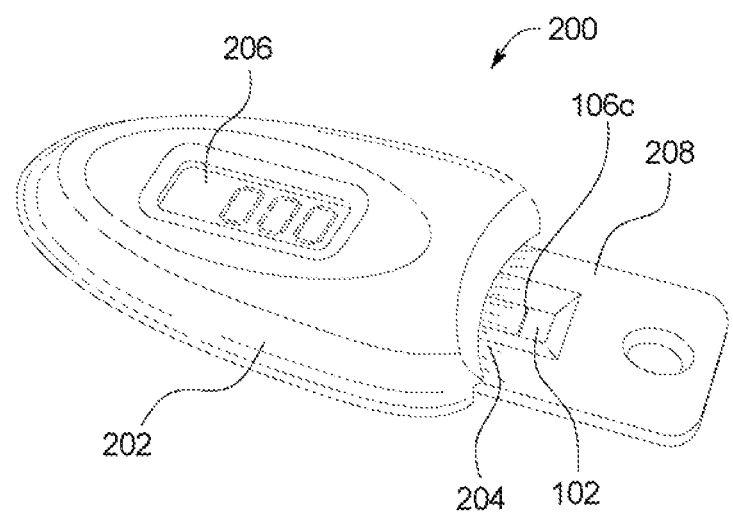
FIG. 2 illustrates a plan view of a device implementing an example single-detector assay reader as disclosed herein.

Referring now to FIG. 1, a schematic diagram of an embodiment of the disclosed assay reader 100 is illustrated. It should be appreciated that in the illustrated embodiment, a body portion of the assay reader (which houses the detector and the associated electronics, as illustrated in FIG. 2, discussed below) and the associated control electronics of the assay test reader are not illustrated for clarity. Thus, the illustrated schematic diagram 100 of the disclosed assay reader includes an assay strip 102 and a detector 104.

The assay strip 102 includes a plurality of regions 106a, 106b, and 106c. In the illustrated embodiment, the regions 106a, 106b, and 106c each contain substances, such as antibodies, disposed on the assay strip 102. The substances may react with analytes contained in a biological fluid, and may cause the regions 106a, 106b, and/or 106c to change intensities or colors in the presence of a particular analyte. In the illustrated embodiments, depending upon the results of the tests performed with the assay strip 102, one or more of the regions 106a, 106b, and 106c may not be visible following application of biological fluid to the assay strip 102 (e.g., if a tested-for analyte is not present in the biological sample applied to the assay strip 102). It should be further appreciated that in the illustrated embodiment, the assay strip 102 is not contained within a housing, casing, or other shell. That is, the illustrated assay strip 102 is inserted directly into the body of the disclosed reader, and is not provided as an assay strip cartridge or other type of encased assay test strip. However, in other embodiments, not illustrated in FIG. 1, it should be appreciated that the assay test strip is enclosed or encased to form an assay test strip cartridge.

The illustrated embodiment of the assay test reader 100 disclosed herein also includes a detector 104. As will be discussed in more detail below, the detector 104 may include a photodiode based detector, an imager, or any other appropriate type of detector. Further, the detector 104 may include an optics 104a to improve light collection efficiency of the detector 104. For example, the optics 104a may include an aperture, such as a slit-shaped aperture or a pin-hole aperture, to enhance the focus and/or signal strength of the light on to the active portion of the detector. In various embodiments, the optics 104a of the detector 104 may be one or more lenses, mirrors, diffractive elements, or apertures, such as the pin-hole or slit-type aperture mentioned above, may be clear, colored, or coated material such as glass or plastic, or may be any other suitable optical device for improving the light collection efficiency and capabilities of the detector 104.

The detector 104 illustrated in FIG. 1 is configured to determine whether a line is present (i.e., whether an analyte present in the biological sample has reacted with a substance, resulting in a visual indication of the reaction) at the portion 104b of the assay strip 102 directly under the detector 104. It should be appreciated that when the detector 104 is in the illustrated position with respect to the assay test strip 102, the detector 104 does not detect the presence of a line (such as the lines illustrated at regions 106a, 106b, or 106c), as the analyzed portion 104b of the assay strip 102 does not include an appropriate substance to react with the biological sample.

The illustrated schematic representation of the assay reader 100 includes arrow 108, which indicates the relative motion of the assay strip 102 with respect to the detector 104. In the illustrated embodiment, the arrow 108 indicates that during use, the assay strip 102 can be moved laterally with respect to the detector 104. It should be appreciated that given such movement, the detector 104 may at various points during the movement of the assay strip 102 detect the presence of lines 106a, 106b, or 106c. It should thus be appreciated that when movement of the assay strip 102 with respect to the body (not shown) and the detector 104 of the assay reader 100 results in portion 104b of the assay test strip 102 which is directly under the detector 104 coinciding with one of the lines 106a, 106b, or 106c, the detector may detect the presence of one of the illustrated lines. The detection of the presence of such a line, which is indicative of the presence of an analyte, is thereafter usable to determine the results of a medical diagnostic test.

Upon detection of an appropriate visual indication of a reaction, such as upon detection of a line at region 106a, 106b, or 106c, the disclosed assay reader sends a signal to associated control electronics (not shown) for processing. This control electronics may include analog processing, such as amplification and filtering, and/or digital processing. The signal may be indicative of a profile of the assay test strip 102, and may include information usable by the control electronics to make a qualitative determination as to the outcome of a medical test. For example, the control electronics may determine that based on a certain pattern of detected lines, the person from whom biological fluid originated is or is not pregnant based on the presence or absence of certain analytes in the person's urine.

In an embodiment, the electronics include at least one display device connected to the detector, such that a signal sent by the detector results in the display device displaying the determined qualitative outcome of the medical test to the user of the assay strip. For example, in an analyte test designed to determine whether a person is pregnant, if the determination is that the person is pregnant, the display device may display the word "pregnant." Alternatively, the display device may display an indication of a quantitative result of a test, such as an indication regarding the intensity of a line of an assay test strip.

Exemplary assays contemplated for use with the assay test readers of the present disclosure include lateral flow assay test strips. Lateral flow assay test strips may comprise a membrane system that forms a single fluid flow pathway along the test strip. The membrane system may include one or more components that act as a solid support for immunoreactions. For example, porous, bibulous or absorbent materials may be placed on a strip such that they partially overlap, or a single material can be used, in order to conduct liquid along the strip. The membrane materials may be supported on a backing, such as a plastic backing. In a preferred embodiment, the test strip includes a glass fiber pad, a nitrocellulose strip and an absorbent cellulose paper strip supported on a plastic backing.

Antibodies that react with the target analyte and/or a detectable label system are immobilized on a solid support provided by the test strip. The antibodies may be bound to the test strip by adsorption, ionic binding, van der Waals adsorption, electrostatic binding, or by covalent binding, by using a coupling agent, such as glutaraldehyde. For example, the antibodies may be applied to the conjugate pad and nitrocellulose strip using standard dispensing methods, such as a syringe pump, air brush, ceramic piston pump or drop-on-demand dispenser. In a preferred embodiment, a volumetric ceramic piston pump dispenser may be used to stripe antibodies that bind the analyte of interest, including a labeled antibody conjugate, onto a glass fiber conjugate pad and a nitrocellulose strip. The test strip may or may not be otherwise treated, for example, with sugar to facilitate mobility along the test strip or with water-soluble non-immune animal proteins, such as albumins, including bovine (BSA), other animal proteins, water-soluble polyamino acids, or casein to block non-specific binding sites.

Any antibody, including polyclonal or monoclonal antibodies, or any fragment thereof, such as the Fab fragment, that binds the analyte of interest, is contemplated for use herein.

An antibody conjugate containing a detectable label may be used to bind the analyte of interest. The detectable label used in the antibody conjugate may be any physical or chemical label capable of being detected on a solid support using a reader, preferably a reflectance reader, and capable of being used to distinguish the reagents to be detected from other compounds and materials in the assay.

Suitable antibody labels are well known to those of skill in the art and include, but are not limited to, enzyme-substrate combinations that produce color upon reaction, colored particles, such as latex particles, colloidal metal or metal or carbon sol labels, fluorescent labels, and liposome or polymer sacs, which are detected due to aggregation of the label. In an embodiment, colloidal gold is used in the labeled antibody conjugate. The label may be derivatized for linking antibodies, such as by attaching functional groups, such as carboxyl groups to the surface of a particle to permit covalent attachment of antibodies. Antibodies may be conjugated to the label using well known coupling methods.

The assay test strip may be any conventional lateral flow assay test strip such as those disclosed in EP 291194 or U.S. Pat. No. 6,352,862. The test strip may comprise a porous carrier containing a particulate labeled specific binding reagent and an unlabelled specific binding reagent.

An assay, as discussed herein, may be configured to test for the presence of one or more analytes in a biological sample applied to the assay. A sample may include, for example, anything which may contain an analyte. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). A liquid sample may refer to a material suspected of containing the analyte(s) of interest, which material has sufficient fluidity to flow through an immunoassay device in accordance herewith. The fluid sample can be used as obtained directly from the source or following a pretreatment so as to modify its character. Such samples can include human, animal or man-made samples. The sample can be prepared in any convenient medium which does not interfere with the assay. Typically, the sample is an aqueous solution or biological fluid as described in more detail below.

A fluid sample (e.g., biological fluid) may refer to a material suspected of containing the analyte(s) of interest, which material has sufficient fluidity to flow through an immunoassay device in accordance herewith. The fluid sample can be used as obtained directly from the source or following a pretreatment so as to modify its character. Such samples can include human, animal or man-made samples. The sample can be prepared in any convenient medium which does not interfere with the assay.

The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte.

Exemplary lateral flow devices include those described in U.S. Pat. Nos. 4,818,677, 4,943,522, 5,096,837 (RE35,306), 5,096,837, 5,118,428, 5,118,630, 5,221,616, 5,223,220, 5,225,328, 5,415,994, 5,434,057, 5,521,102, 5,536,646, 5,541,069, 5,686,315, 5,763,262, 5,766,961, 5,770,460, 5,773,234, 5,786,220, 5,804,452, 5,814,455, 5,939,331, and/or 6,306,642.

An analyte can be any substance for which there exists a naturally occurring analyte specific binding member or for which an analyte-specific binding member can be prepared. e.g., carbohydrate and lectin, hormone and receptor, complementary nucleic acids, and the like. Further, possible analytes include virtually any compound, composition, aggregation, or other substance which may be immunologically detected. That is, the analyte, or portion thereof, will be antigenic or haptenic having at least one determinant site, or will be a member of a naturally occurring binding pair.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof (see, e.g., U.S. Pat. Nos. 4,366,241; 4,299,916; 4,275,149; and 4,806,311).

In an embodiment, a sample receiving zone on the surface of a lateral flow assay test strip accepts a fluid sample that may contain one or more analytes of interest. In an embodiment, the sample receiving zone is dipped into a fluid sample. A label zone is located downstream of the sample receiving zone, and contains one or more mobile label reagents that recognize, or are capable of binding the analytes of interest. Further, one or more test regions may be disposed downstream from the label zone, and may contain one or more test and/or control zones. The test zone(s) generally contain means which permit the restraint of a particular analyte of interest in each test zone. Frequently, the means included in the test zone(s) comprise an immobilized capture reagent that binds to the analyte of interest. Generally the immobilized capture reagent specifically binds to the analyte of interest. Thus, as the fluid sample flows along the matrix, the analyte of interest will first bind with a mobilizable label reagent in the label zone, and then become restrained in the test zone.

In an embodiment, the sample receiving zone may be comprised of an absorbent application pad. Suitable materials for manufacturing absorbent application pads include, but are not limited to, hydrophilic polyethylene materials or pads, acrylic fiber, glass fiber, filter paper or pads, desiccated paper, paper pulp, fabric, and the like. For example, the sample receiving zone may be comprised of a material such as a nonwoven spunlaced acrylic fiber.

The sample receiving zone may be comprised of any material from which the fluid sample can pass to the label zone. Further, the absorbent application pad can be constructed to act as a filter for cellular components, hormones, particulate, and other certain substances that may occur in the fluid sample. Application pad materials suitable for use by the present disclosure also include those application pad materials disclosed in U.S. Pat. No. 5,075,078.

In a further embodiment, the sample receiving zone may be comprised of an additional sample application member (e.g., a wick). Thus, in one aspect, the sample receiving zone can comprise a sample application pad as well as a sample application member. Often the sample application member is comprised of a material that readily absorbs any of a variety of fluid samples contemplated herein, and remains robust in physical form. Frequently, the sample application member is comprised of a material such as white bonded polyester fiber. Moreover, the sample application member, if present, is positioned in fluid-flow contact with a sample application pad.

In an embodiment, the label zone material may be treated with labeled solution that includes material-blocking and label-stabilizing agents. Blocking agents include, for example, bovine serum albumin (BSA), methylated BSA, casein and nonfat dry milk. Stabilizing agents are readily available and well known in the art, and may be used, for example, to stabilize labeled reagents.

The label zone may contain a labeled reagent, often comprising one or more labeled reagents. In many of the presently contemplated embodiments, multiple types of labeled reagents are incorporated in the label zone such that they may permeate together with a fluid sample contacted with the device. These multiple types of labeled reagent can be analyte specific or control reagents and may have different detectable characteristics (e.g., different colors) such that one labeled reagent can be differentiated from another labeled reagent if utilized in the same device. As the labeled reagents are frequently bound to a specific analyte of interest subsequent to fluid sample flow through the label zone, differential detection of labeled reagents having different specificities (including analyte specific and control labeled reagents) may be a desirable attribute. However, frequently, the ability to differentially detect the labeled reagents having different specificities based on the label component alone is not necessary due to the presence of test and control zones in the device, which allow for the accumulation of labeled reagent in designated zones.

The labeling zone may also include control-type reagents. These labeled control reagents often comprise detectible moieties that will not become restrained in the test zones and that are carried through to the test region and control zone(s) by fluid sample flow through the device. In a frequent embodiment, these detectible moieties are coupled to a member of a specific binding pair to form a control conjugate which can then be restrained in a separate control zone of the test region by a corresponding member of the specific binding pair to verify that the flow of liquid is as expected. The visible moieties used in the labeled control reagents may be the same or different color, or of the same or different type, as those used in the analyte of interest specific labeled reagents. If different colors are used, ease of observing the results may be enhanced.

The test region may include a control zone for verification that the sample flow is as expected. Each of the control zones comprise a spatially distinct region that often includes an immobilized member of a specific binding pair which reacts with a labeled control reagent. In an occasional embodiment, the procedural control zone contains an authentic sample of the analyte of interest, or a fragment thereof. In this embodiment, one type of labeled reagent can be utilized, wherein fluid sample transports the labeled reagent to the test and control zones; and the labeled reagent not bound to an analyte of interest will then bind to the authentic sample of the analyte of interest positioned in the control zone. In another embodiment, the control line contains antibody that is specific for, or otherwise provides for the immobilization of, the labeled reagent. In operation, a labeled reagent is restrained in each of the one or more control zones, even when any or all the analytes of interest are absent from the test sample.

Since the devices of the present disclosure may incorporate one or more control zones, the labeled control reagent and their corresponding control zones are preferably developed such that each control zone will become visible with a desired intensity for all control zones after fluid sample is contacted with the device, regardless of the presence or absence of one or more analytes of interest. In one embodiment, a single labeled control reagent will be captured by each of the control zones on the test strip. Frequently, such a labeled control reagent will be deposited onto or in the label zone in an amount exceeding the capacity of the total binding capacity of the combined control zones if multiple control zones are present. Accordingly, the amount of capture reagent specific for the control label can be deposited in an amount that allows for the generation of desired signal intensity in the one or more control zones, and allows each of the control zones to restrain a desired amount of labeled control-reagent. At the completion of an assay, each of the control zones preferably provide a desired and/or pre-designed signal (in intensity and form).

In an embodiment, each control zone will be specific for a unique control reagent. In this embodiment, the label zone may include multiple and different labeled control reagents, equaling the number of control zones in the assay, or a related variation. Wherein each of the labeled control reagents may become restrained in one or more pre-determined and specific control zone(s). These labeled control reagents can provide the same detectible signal (e.g., be of the same color) or provide distinguishable detectible signals (e.g., have different colored labels or other detection systems) upon accumulation in the control zone(s).

In an embodiment, the labeled control reagent comprises a detectible moiety coupled to a member of a specific binding pair. Typically, a labeled control reagent is chosen to be different from the reagent that is recognized by the means which are capable of restraining an analyte of interest in the test zone. Further, the labeled control reagent is generally not specific for the analyte. In a frequent embodiment, the labeled control reagent is capable of binding the corresponding member of a specific binding pair or control capture partner that is immobilized on or in the control zone. Thus the labeled control reagent is directly restrained in the control zone.

The use of a control zone is helpful in that appearance of a signal in the control zone indicates the time at which the test result can be read, even for a negative result. Thus, when the expected signal appears in the control line, the presence or absence of a signal in a test zone can be noted.

Test zones of the present description include means that permit the restraint of an analyte of interest. Frequently, test zones of the present description include a ligand that is capable of specifically binding to an analyte of interest. Alternatively, test zones of the present description include a ligand that is capable of specifically binding the labeled reagent bound to an analyte of interest. In practice, a labeled test reagent binds an analyte of interest present in a fluid sample after contact of the sample with a representative device and flow of the fluid sample into and through the label zone. Thereafter, the fluid sample containing the labeled analyte progresses to a test zone and becomes restrained in the test zone. The accumulation of labeled analyte in the test zone produces a detectible signal. Devices may incorporate one or more test zones, each of which is capable of restraining different analytes, if present, in a fluid sample. Thus, in representative embodiments two, three, four, five or more (labeled) analytes of interest can be restrained in a single or different test zones, and thereby detected, in a single device.

The present devices may optionally further comprise an absorbent zone that acts to absorb excess sample after the sample migrates through the test region. The absorbent zone, when present lies in fluid flow contact with the test region. This fluid flow contact can comprise an overlapping, abutting or interlaced type of contact. In an occasional embodiment, a control region (end of assay indicator) is provided in the absorbent zone to indicate when the assay is complete. In this embodiment, specialized reagents are utilized, such as pH sensitive reagents (such as bromocresol green), to indicate when the fluid sample has permeated past all of the test and control zones.

As discussed above, the disclosed assay test reader may include one or more sensors, such as the detector 104 illustrated in FIG. 1, which operate to determine whether a visual characteristic of an assay indicates the presence of an assay. The detectors may be any suitable type of detector, such as a photo-detector including a PIN-diode based detector, a CCD sensor, a CMOS sensor, an InGaAs detector, or any other type of photo-detector. Alternatively or in addition, the sensor may be configured to sense another characteristic of an assay test strip, such as an electro-magnetic characteristic of the strip, a physical characteristic of the strip (such as density or moisture retention), or any other suitable characteristic of the strip. These detectors may be included within the body of the disclosed assay test reader. In one embodiment, the one or more detectors of the disclosed assay reader may be affixed or connected to a body of the assay reader.

One or more light sources may be utilized in conjunction with the one or more detectors such that during use, light from the light source or sources falls upon a portion of the porous carrier, such as the portion 104b of the assay strip 102 of FIG. 1, and is reflected or transmitted to the respective detector. For example, the light source may be an illuminator configured to generate light and to emit it in the direction of the portion 104b of the assay test strip to be examined. The detector may then generate a current roughly proportional to the amount of light falling upon it. This current can be converted to a voltage signal by a feeding it through a resistor, or a trans-impedance amplifier, or by timed integration through a capacitor. The amount of light reaching the detector may depend upon the amount of colored particulate label present and therefore the amount of analyte. In this way, the amount of analyte present in the sample may be determined. An exemplary method of optically determining the analyte concentration using one or more detectors is described more fully in EP 653625.

The disclosed detectors may include PIN-diode detectors as are well known in the art. In such PIN-diode detectors, photons entering the PIN-diode create a flow of current proportional to the amount of photons received through the diode and into a resistor, a transimpedance amplifier, or through a capacitor with time gating. In the event that a detected photon creates or enables flow of current, the non-zero current flowing through the diode causes a non-zero current, which is detectable by appropriate electronics coupled to the PIN-diode. For example, control electronics may be configured to receive signals from the detector indicative of an amount of detected light, and may be configured to determine that such signals indicate a presence or an absence of an analyte reaction as described in more detail below.

Alternatively or in addition, the disclosed detectors may include imagers configured to generate similar signals indicative of a presence or an absence of an analyte reaction. In such imagers, potentially along with a light source, detects the presence or absence of light at an analyzed portion of the assay strip. The imager converts this detected color into a digital signal (such as based on a magnitude of a generated voltage) and outputs that signal to appropriate electronics for handling. For example, control electronics similar to those described above with respect to the PIN-diode based detector may convert a plurality of voltages into a signal indicative of a presence or an absence of an analyte reaction.

It should be appreciated that a PIN-diode based detector may be less costly and more easily implemented than a CMOS-based imager. Specifically, the cost of the detector itself may be less for a PIN-diode based detector than for a CMOS-based imager, and the cost of the control or supporting electronics required to handle the signals generated by the detector may also be lower for the PIN-diode based detector than for a CMOS-based imager. However, it should be appreciated that either type of detector (as well as any other type of known detector not explicitly discussed herein) is equally applicable in the context of the disclosed assay reader.

Any device which is compatible for detecting the presence of analyte reactions (i.e., lines) on an assay test strip, such as a PIN detector, a CMOS imager, or another type of reflectance or fluorescence reader for determining the assay result is contemplated for use with the assay reader described herein. Certain suitable detector devices are known to those of skill in the art (see, e.g., U.S. Pat. Nos. 5,658,801, 5,656,502, 5,591,645, 5,500,375, 5,252,459, 5,132,097). Reflectance and other readers, including densitometers and transmittance readers, are known to those of skill in the art (see, e.g., U.S. Pat. Nos. 5,598,007, 5,132,097, 5,094,955, 4,267,261, 5,118,183, 5,661,563, 4,647,544, 4,197,088, 4,666,309, 5,457,313, 3,905,767, 5,198,369, 4,400,353). The use of such detectors is achieved by mounting or otherwise affixing such detectors to the body of the assay reader, and enabling the test strip to move with respect to the body/detector combination, as described above.

Reference is now made to FIG. 2, which illustrates a plan view of an assay test strip reader as disclosed herein. Specifically, FIG. 2 illustrates an assay test strip reader 200 including a body 202, an assay strip insertion portion 204, and a display or audio/visual indicator 206.

In the illustrated embodiment, an assay test strip 102 is encased in a housing, casing, or shell 208. That is, the illustrated assay test strip 102 is contained within the shell 208 to form a cartridge insertable in the reader. In one embodiment, the housing 208 is a plastic shell configured to protect the assay strip 102 from accidental contamination and damage, and configured to prevent biological fluid on the strip 102 from entering the body 202 of the assay test strip reader or from touching the skin of a user of the reader 200. The housing may alternatively be made another inert material, other than plastic, that does not interfere with the assay procedure.

In the illustrated embodiment, an assay test strip 102, similar to the assay test strip 102 of FIG. 1, is illustrated as encased in a housing 208, which housing is partially inserted in the reader 200. The insertion portion 204 of the body 202 is sized to receive the housing 208 of the assay test strip 102, such as by being slightly larger than the cross section of housing 208 of the assay test strip 102.

It should be appreciated that the disclosed assay reader 200 may be configured to receive an assay strip 102 which is not encased in a housing such as housing 208. In such an embodiment embodiment, the assay strip insertion portion 204 is sized to receive the assay strip 102 without any housing.

The amount of the test strip 102 which is visible through the housing or shell 208 may vary based, for example, on a quantity of antibody regions or portions on the strip. The housing 208 may be made from any suitable material, including plastic or other suitable material. Further, the housing 208/test strip 102 assembly may be reusable, such as by replacing the test strip 102 within the housing 208. Alternatively, the housing 208/test strip 102 assembly may be disposable, wherein the entire assembly is disposed after use.

In the illustrated embodiment, the detector included within the body 202 of the assay test strip reader 200 is not visible, and thus is not shown. In one embodiment, light from an illuminator or other light source contained within the body 200 may be visible exiting the insertion portion 204. This light may enable the detector to obtain an accurate reading of the lines, such as line 106c, that are visible on the assay test strip 102 following application of biological fluid.

The assay reader disclosed herein may be configured to operate with any of the different assay test strips described above. Moreover, in embodiments wherein a housing 208 is included for use with an assay test strip, an appropriate housing or shell may be provided which can operate with any of the different types of assay test strips described above. In an embodiment, the disclosed reader operates with another diagnostic tool other than an assay test strip. That is, any diagnostic medium which could indicate the presence or absence of a diagnostic condition may be inserted into the body of the disclosed reader, and the sensor contained in the disclosed reader may be utilized to detect the presence or absence of the diagnostic condition.

The disclosed assay reader utilizes at least one detector, positioned within the body of the reader, to determine the condition of an assay test strip following an appropriate analyte-reaction test. Specifically, by affixing the detector to the body, the disclosed reader relies on the motion of the test strip relative to the body/detector combination to enable the detector to accurately detect the results of the test. For example, if a single detector is used, it is fixedly attached to the body such that the detector can detect the optical condition of the test strip.

A test strip may be inserted or removed from within the body, such that the test strip moves relative to both the body and the detector. In an embodiment wherein a single detector is utilized, the motion of the test strip into and out of the body causes the detector to scan a linear (i.e., a one-dimensional) portion of the test strip. As the test strip is scanned along its length and the detector detects the profile of the optical response from a one-dimensional portion of the test strip, a profile of the optical response representing analyte reactions along the one-dimensional portion of the test strip is created, the profile including a representation of the various optical characteristics of the strip. In an embodiment, the disclosed reader stores (e.g., in the control electronics) data representative of the one-dimensional profile of the optical response representing analyte reactions along the one-dimensional portion of the test strip.

Figure 3:
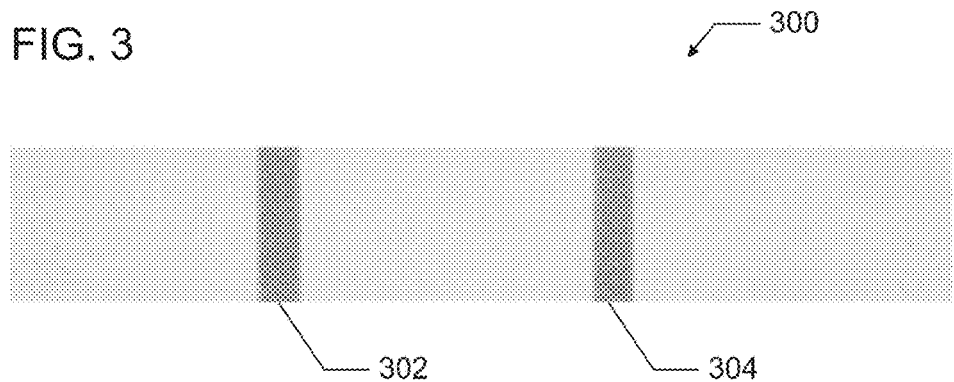
FIG. 3 illustrates a 2-dimensional (2D) image representing an assay strip having two test lines, where the x and y positions of the 2D image correspond to positions on the assay strip, and where the signal strength is represented by the intensity of the x and y location.

FIG. 3 is an image of an example assay test strip 300 in which two test lines 302 and 304 are present. Specifically, FIG. 3 is a two-dimensional image of an assay test strip 300 indicating both the length and the width of the assay test strip 300, and also indicating where on the assay test strip the two analyte reaction regions (i.e., the two test lines 302 and 304) are positioned. In the illustrated embodiment, the two test lines 302 and 304 are indicated by a darker color of the assay test strip at the portion of the strip containing the two test lines.

Figure 4:
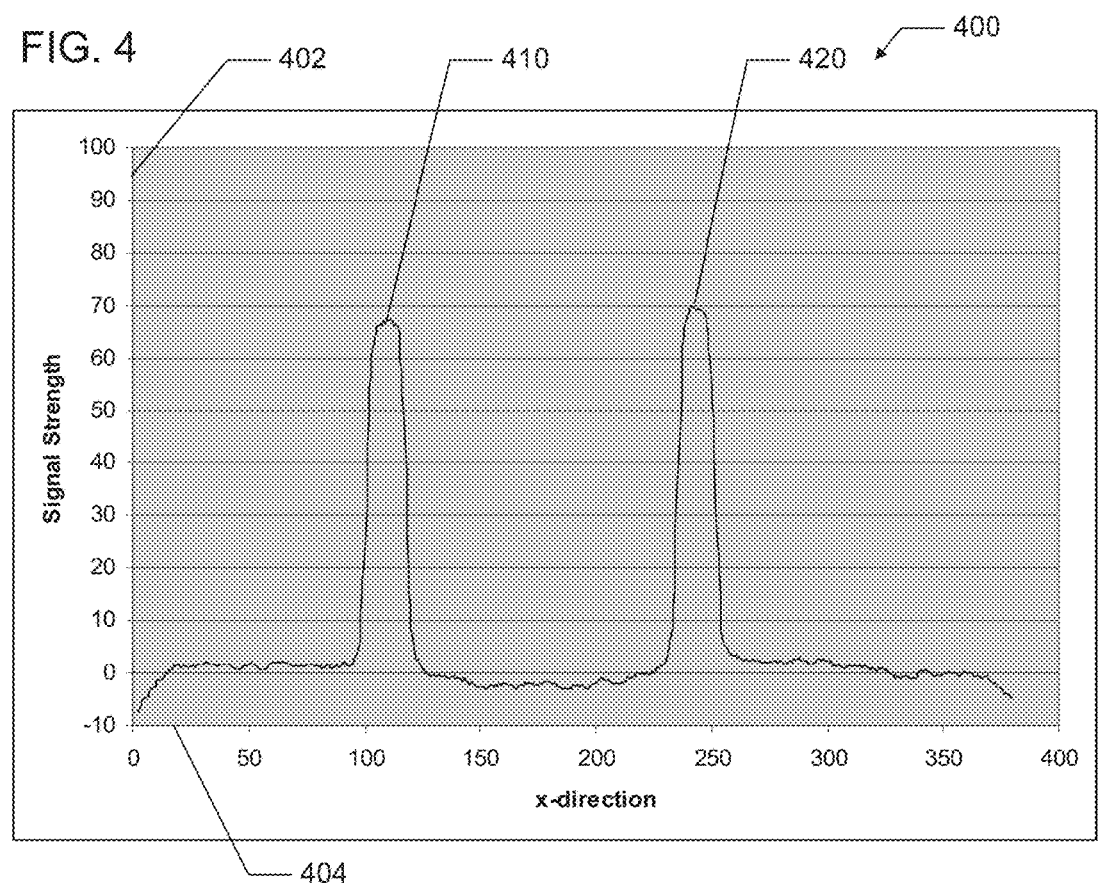
FIG. 4 illustrates a profile of an optical response representing analyte reactions along a one-dimensional (1D) portion of an assay strip having two test lines, where the vertical axis represents the detected signal strength and the horizontal axis represents the position of the assay strip.

FIG. 4 illustrates an example profile representing analyte reactions along a one-dimensional portion of a test strip 400, such as the test strip 300 illustrated in FIG. 3, inserted in the an embodiment of the disclosed reader. In the illustrated embodiment, the vertical axis 402 of FIG. 4 represents the strength of a signal generated by a detector or sensor of the disclosed reader. The horizontal axis 404 of FIG. 4 represents the position of the inserted test strip (such as test strip 300) that corresponds with the detected signal. In the illustrated embodiment, the test strip inserted in the disclosed reader indicates an analyte reaction at a position corresponding to slightly more than the "100" position of the horizontal axis, indicated by numeral 410, and also indicates an analyte reaction at a position slightly less than the "250" position of the horizontal axis, indicated by numeral 420. It should be appreciated that the analyte reactions illustrated in FIG. 3 are represented in FIG. 4 by the relatively high signal generated at these two positions 302 and 304 of the assay test strip 300 discussed above. Thus, it should be appreciated that the positions 302 and 304 of the test lines of FIG. 3 may correspond to the position 410 which is slightly more than "100" of FIG. 4, and to the position 420 which is slightly less than "250" of FIG. 4.

In an embodiment, the control electronics of the disclosed reader store data indicative of the detected profile. For example, the control electronics of the disclosed reader may store data indicative of the profile illustrated in FIG. 4. This data may be stored in any appropriate way as is well known in the art, such as by storing a plurality or ordered pairs representing an x-coordinate (e.g., a position on the assay strip) and a y-coordinate (e.g., a value indicative of a magnitude of a detected signal). Based on the created profile, control electronics coupled to the detector may determine at least one outcome (or data indicative of an outcome) of the test, such as by determining that the test resulted in a "positive" or "negative" result. For example, this determination may be made based on those portions of the profile which reflect relative signals, and thus indicate that a line is present on the scanned assay test strip.

In various embodiments, the control electronics disclosed herein receive signals from any sensor(s) disposed within the body of the reader, which are proportional to an amount of a measured characteristic. For example, if a measured characteristic of the reader is the color of a line on an assay test strip, the sensor may output a signal proportional to the intensity of such color. Likewise, if a measured characteristic of the reader is a magnetic field induced by the test strip, the sensor may output a signal proportional to the strength of the magnetic field. This proportional signal may enable the control electronics to discern a result of the test based, at least in part, on an amount of a detected signal (i.e., as opposed to merely the presence of a detected signal.

In an embodiment, the disclosed reader is configured to make a qualitative determination about the outcome of a test (e.g., at "positive" or "negative" outcome) based on the existence of a signal sensed by a sensor. In another embodiment, the disclosed reader is configured to make a quantitative determination (e.g., a determination as to an analyte concentration within a sample) which is useful in determining a condition of the provider of the sample. For example, a quantitative determination as to the blood-glucose concentration of a subject may be made by the disclosed reader based on a magnitude of a signal generated by a sensor.

The control electronics of the disclosed assay strip reader may be aware of the pattern of antibody regions on an inserted assay test strip in order to determine a qualitative result of a test. For example, the control electronics may be aware that it should expect the detection of two or three different lines depending on a particular result of the test. Moreover, the control electronics may be aware, roughly, of the position of the expected lines within the assay test strip. For example, the control electronics may expect a first line, recognize that a second line may or may not be detected, and expect a third line, wherein the second line is approximately halfway between the first line and the third line. In this embodiment, the control electronics may verify the correctness of the functioning of the test by ensuring that if only two lines are present, the amount of space between the two lines is roughly twice the amount of space between each of three expected lines. In an embodiment, the assay test reader determines that it is functioning properly simply by counting the number of detected lines and white spaces between lines to ensure that the proper reactions have occurred given the particular type of test being performed.

This awareness in the control electronics may be pre-programmed into the control electronics, such that particular control electronics are configured to detect results of particular tests. Alternatively, the control electronics of an assay test reader as disclosed herein may be programmable, such as by connecting the assay reader device to a computerized device so as to enable the computerized device to upload instructions to the assay test strip reader.

In an embodiment, the control electronics are unaware about the type of profile to expect when scanning an assay test strip. For example, the control electronics may simply receive data indicative of a profile of an optical response representing analyte reactons along a one-dimensional portion of the assay test strip, and may either output the raw data directly to a display device, or may upload that data to a remote computer device for handling. Thus, in these embodiments, the control electronics may only need to be able to handle raw profile data, such as by outputting the raw data or by uploading the raw data to a remote computing device.

The optical signals measured by the detector may be reflectance or fluorescent signals. As discussed above, the detector may be any suitable type of detector, such as a PIN-diode based detector, a CMOS imager, or another type of detector. The detector may include or be associated with an illuminator or other light source to enable the detector to accurately read the assay test strip inserted in the assay reader. The detector may be oriented so as to directly face a test surface of the test strip, or may be oriented to detect optical characteristics of the assay test strip based on one or more reflections of the surface of the test strip. The detector may be powered by an on-board battery or may be powered based on an always-on power source, such as power from a standard wall outlet. The detector may provide raw signals, such as a voltages, directly to the associated electronics, further amplify or filter these signals, or may convert these signals to digital data indicative of the detected optical properties of the test strip and thereafter provide that digital data to the associated electronics for further processing.

The detector as described herein may include a plurality of detectors, such as a plurality of detectors arranged as an array of detectors. In such an embodiment, each of the plurality of detectors may simultaneously determine optical data about the test strip, such that for each position of the test strip during insertion and/or removal from the body, a plurality of different data points are collected. It should be appreciated that with such an array of detectors, the disclosed reader may enable the creation of data indicative of a two-dimensional portion of the test strip. The width of this two-dimensional portion may be based on the width of the array of detectors, and the length of this two-dimensional portion may be based on the distance the test strip is slid or otherwise moved with respect to the detector within the body.

In one embodiment, the reader disclosed herein creates a two-dimensional image by creating a plurality of images (whether one-dimensional images or two-dimensional images) in a time-lapse fashion, and by thereafter stacking, stitching, or otherwise combining the images on top of one another. In this stitching environment, the disclosed system may enable accurate recreation of distances within the test strip, such as by calculating the appropriate location for each stacked or stitched image based on a known width of the strip, length of movement of the strip, and/or delay between time-lapsed image captures.

The disclosed assay reader may include one or more display devices configured to display information about the scanned test strip to a user of the reader. For example, one or more LCD, LED, or other type of electronic display devices may be connected to the electronics and/or the detector to display information indicative of an outcome of the scan of the test strip. This information may include an outcome of a test (such as a "positive" or "negative" outcome), a number indicative of a characteristic of biological fluid tested (such as an amount or concentration of a particular substance in the fluid), or other data indicative of a characteristic of the assay strip.

In one embodiment, the display device is a device configured to output a visual indication of a result of a test. For example, the display device could be the LCD, LED, or other type of electronic display device discussed above. In another embodiment, the display device is a device which non-electronically displays an indication of a result of a test. For example, the display device may include a substrate configured to change colors depending on the characteristics of the assay test strip detected by the one or more sensors within the body of the disclosed reader.

In one embodiment, the disclosed display device may include an audio output device configured to output an audio signal indicative of a result of a test. For example, the display device may be configured to emit an audible tone if a designated result of the test is achieved—such as if a test results in a "positive" outcome. If the disclosed reader is configured to make a quantitative determination of the outcome of the test, the audible tone may vary in intensity, length, pitch, or another characteristic to indicate the quantitative determination regarding the outcome of the test. These audible tones may include synthesized speech configured to generate the sound of words understandable by an operator of the disclosed reader.

In a further embodiment, the assay reader is connectable to an existing computing device separate from the assay reader itself, such as a personal computer, via a wired (e.g., USB, serial, or other wired technology) or wireless (e.g., WiFi, Bluetooth, or other wireless technology) connection. In this embodiment, data about the state of the assay strip may be uploaded from the reader to the separate computing device. Upon such uploading, the separate computing device may perform additional processing on the data, may store the data, may send the data to a third party such as a health care professional or other health care entity, or may otherwise handle or analyze the data. In this embodiment, the reader itself may not include a display; rather, the display device of the personal computer may be relied on to display the detected information. In various embodiments, the separate computing device to which the reader connects may include a special-purpose electronic device, a personal digital assistant ("PDA"), a cellular telephone, a laptop computer, a tablet computer, an interactive television system including a set-top box, or any other appropriate type of microprocessor-based device.

The disclosed reader utilizes the motion of the test strip relative to the body/detector assembly to form or construct the profile of the analyte regions on the test strip. That is, the disclosed reader overcomes certain of the drawbacks of prior art readers by fixing the location of the detector with respect to the body, and by determining a one- or two-dimensional profile of the assay strip based on movement of the assay strip itself with respect to the detector. This motion may occur with the insertion and/or removal of the assay strip from the body of the reader, such as with the insertion and removal by a user or operator of the reader.

Alternatively, insertion of the test strip by a user may load a spring mechanism within the body of the reader. Release of the spring mechanism may push the test strip out of the body of the reader, and the detector may scan the strip as it is pushed out of the body of the reader. Release of the spring mechanism may be achieved by a mechanical device such as a switch, or by an opto-electronic device such as an electronically-triggered switch controlled by the electronics of the reader. For instance, upon the electronics confirming that the test strip is properly inserted in the reader, the electronics may trigger a switch to release the spring mechanism, ejecting the test strip and enabling the detector to scan the analyte profile of the test strip.

In one embodiment, the relative position of the lines representing reactions of analytes in a biological fluid with a substance disposed on the assay test strip is important to the outcome of a particular test. For example, if three different regions are present on a test strip, it may not be enough to simply know that two of the regions reacted with analytes in the sample to form visible lines. Rather, it may be important to know which of the two lines are visible, and thus which of the two lines reacted with analytes in the sample. Such determinations may be made based on the relative positions of each of the lines to one another. In an embodiment, an analyte test strip (or a cartridge into which such a strip is inserted) may include an encoder usable by the control electronics to determine the relative position of the strip (or the cartridge) with respect to the detector at a given point in time.

For example, an encoder may include a plurality of printed marks on the test strip (or the cartridge) which are read by a detector, such as one of the detectors in an array of detectors included in the disclosed reader. The control electronics may utilize the detected printed marks to determine the position of the test strip within the body at a point in time. For example, a test strip (or cartridge) may include an encoder having markings every three millimeters along the length of the cartridge. By sensing these markings with a detector in the reader, the disclosed control electronics may be able to distinguish between a visible line at a first region (such as at a region at a "zero" position) and a visible line at a second region (such as a region six millimeters beyond the "zero" position). The ability to so distinguish between the relative positions of the analyte regions may enable the reading of more complex tests to be automated in a simple, affordable, portable device.

In such an embodiment, wherein an encoder is included, the disclosed reader may also be able to determine the visible widths of various analyte regions (either relative to one another or absolutely) based on the detection of various markings of the encoder. Thus, for tests whose results depend upon the relative widths of the various analyte regions, the disclosed reader can provide accurate analysis of the results of the tests while minimizing the potential for human error.

The disclosed encoder may also enable the disclosed reader to accurately determine whether a signal is present at a designated location on an assay test strip. For example, if a designated region of the assay test strip is configured to indicate the presence or absence of an analyte in a sample, the encoder may enable the reader to determine when a detector is analyzing that designated region of the assay test strip. If, based on the encoder, the disclosed reader determines that the detector is analyzing the designated region, the reader may determine with certainty whether the designated region of the assay test strip reacted with the sample, and thus whether the tested-for analyte is present. Thus, the disclosed encoder can enable the reader to determine whether a designated portion of the assay test strip is being analyzed by the detector.

Alternatively or in addition, the disclosed reader may utilize an encoder such as described above to linearize the motion of the assay test strip within the reader. For example, the encoder may enable the control electronics, which are coupled to the detector, to construct an accurate representation of the color properties of the assay test strip, including an accurate representation of the spacing of the detected regions, by utilizing the encoder to linearize the results. For example, if an encoder includes a mark every two millimeters, the disclosed reader may rely on those marks to construct a representation of the analyte reaction regions of the test strip regardless of the speed with which the test strip was passed through the reader. Even if the first four millimeters of a test strip are inserted and/or removed more quickly or more slowly than the remainder of the test strip, the control electronics can utilize the detected encoder marks to construct an accurate representation of the colors on the test strip.

In an embodiment, an encoder such as the encoder described herein can be utilized to identify the test strip from among a plurality of different test strips. For example, the disclosed encoder could be disposed on the test strip as a barcode which identifies the type of test enabled by the strip, the name of the individual whose sample is applied to the test strip, information required to calibrate the test strip, assay lot information, or other suitable information about the particular test implemented by the test strip. Alternatively, the encoder may covey such information without being displayed as a bar code—that is, the information may be conveyed in some other suitable way based on the detected marks of the encoder disposed on the assay test strip. It should be appreciated that any suitable information may be conveyed by the encoder, and any suitable use of that information may be made by the disclosed reader.

In an embodiment, the disclosed reader is configured to detect the color properties of an inserted assay strip upon the strip being inserted, removed, or both inserted and removed. For example, if the disclosed reader is configured to detect the characteristics of an assay test strip upon both insertion and removal, the control electronics may utilize the insertion or the removal as an error-checking mechanism to ensure that the same information is detected upon both insertion and removal. Alternatively the disclosed reader may utilize the data detected upon insertion and removal to construct a stronger profile of the assay strip, or to construct a profile of the assay test strip which contains more data, making the profile more accurate and/or more reliable.

In an embodiment, such as the embodiments discussed above, the encoder disclosed herein is configured to be detected by an optical detector, such as a PIN-diode. In another embodiment, the encoder is not optically detectable, but rather is detectable using some other type of detection mechanism. For example, the disclosed encoder may be electrically detectable, electromagnetically or may be detectable based on an electromagnetic emission of the encoder. In another embodiment, the disclosed encoder relies on one or more potentiometers to determine the position of the assay test strip within the body of the reader. For example, one or more linear or rotary potentiometers is positioned within the body of the reader, such that upon an assay test strip being inserted in the reader, the assay test strip engages the potentiometer. Upon engaging the potentiometer, the assay test strip displaces at least one element of the potentiometer during insertion and/or removal of the test strip from the body of the reader. During insertion and/or removal, the engaging element of the potentiometer is displaced proportionately to the amount of displacement of the assay test strip within the body of the reader. The potentiometer detects the amount of displacement, which detected amount of displacement can be utilized by the control electronics to determine the position of the assay test strip within the body of the reader. Thus, it should be appreciated that a potentiometer, arranged as described, can function as an electro-mechanical encoder and can enable the disclosed reader to ascertain the position of the test strip within the reader during insertion and removal of the test strip.

In an embodiment, the reader disclosed herein includes an on/off switch or another manually actuatable mechanism by which the reader is turned on and/or off. In another embodiment, the disclosed reader is turned on upon the insertion of the test strip into the reader. For example, the disclosed reader may be configured to be powered off, or placed in a low-power state, until and unless a test strip is inserted in the body of the reader. Upon insertion of the test strip in the body of the reader, the reader may be powered on for use. In an embodiment, the reader is powered off, or placed in a low-power state, upon the test strip being removed from the reader. In another embodiment, the reader remains powered on for a designated amount of time after the detection of the color properties of the strip, such as to enable a user to read the display device and any indication of the results of the test contained thereon. In summary, the disclosed assay test strip reader analyzes the optical properties of an assay test strip, after that test strip has been utilized to conduct an analyte detection test, to determine the results of the test. The strip is inserted into the body of the reader, and the motion of the strip relative to one or more detectors connected to (and immovable with respect to) the body of the reader enables the disclosed system to create a one- or two-dimensional profile of the test strip. Control electronics coupled to the detector may analyze the profile and provide feedback to a user of the assay strip reader. This low cost alternative to expensive, motorized scanning devices enables a reader which can accurately detect a plurality of analyte regions on a test strip and can therefore accurately output data indicative of the outcome of the test.

In an embodiment, the disclosed reader is not configured to have the assay strip inserted into a body of the reader. In this embodiment, one or more sensors or detectors are configured to detect characteristics of an assay strip without the assay strip being inserted into the body of the reader based on the relative motion of the assay strip with respect to the reader. For example, the disclosed reader may be movable by a human operator over an assay test strip, such as would be done with a scanning wand. Alternatively, the disclosed reader may be stationary, and a human operator may move the assay strip over the reader, such as is done when scanning a bar-code at a supermarket checkout station. Thus, it should be appreciated that in various embodiments, the assay test strip is not insertable in the body of the reader, but the reader is nonetheless configured to scan the assay test strip to determine any reactions which have occurred on the assay test strip.

It should be understood by those skilled in the art that various modifications, combinations, sub-combinations and alterations may occur depending on design requirements and other factors insofar as they are within the scope of the appended claims or the equivalents thereof.

The invention is claimed as follows:

1. A system comprising:
   an assay test strip including a test portion and an encoder portion, the test portion including at least one analyte reaction section, the encoder portion including a plurality of optically detectable markings each at one of a plurality of known positions along a length of the assay test strip;
   an assay test strip reader comprising a body sized to receive the assay test strip;
   at least one detector fixedly connected to the body, the at least one detector positioned within the body such that an inserting of the assay test strip or a removing of the assay test strip by an operator, which results in movement of the assay test strip with respect to the body and the at least one detector, causes the at least one detector to detect signals from different points along the length of the assay test strip, the at least one detector configured to detect encoder optical signals indicative of a position along the length of the assay test strip that is positioned in a field of view of the at least one detector and to detect analyte optical signals indicative of a reaction of at least one analyte at the different points along the length of the assay test strip;
   at least one light source associated with the at least one detector, the at least one light source configured to illuminate at least a portion of the assay test strip adjacent to the at least one detector; and
   control electronics coupled to the at least one detector, the control electronics configured to:
      receive the analyte optical signals and the encoder optical signals from the at least one detector,
      for particular ones of the analyte optical signals:
         determine a magnitude of the analyte optical signal detected by the detector,
         determine, using at least one of the encoder optical signals, the position along the length of the assay test strip that was in the field of view of the detector at a time of detection of the analyte optical signal, and
         store a data pair including a first value indicating the position along the length of the assay test strip and a second value indicating the magnitude of the analyte optical signal,
      determine a distance between the known positions of the optically detectable markings of the encoder portion;
      use the determined distance and the data pairs to generate a linearized representation of a spacing of the magnitudes of the analyte optical signals along the length of the test strip, and
      determine a result in response to comparing the linearized representation to an expected position of analyte optical signals.

2. The system of claim 1, wherein each of the at least one detector is an optical detector.

3. The system of claim 1, further comprising at least one audio/visual indicator affixed to the body, wherein the control electronics are further configured to cause the at least one audio/visual indicator configured to output an audio/visual representation of the result.

4. The system of claim 1, wherein the result indicates a qualitative result of an analyte test.

5. The system of claim 1, wherein the at least one detector includes at least one PIN-diode detector.

6. The system of claim 1, wherein the at least one detector includes at least one CMOS imager.

7. The system of claim 1, wherein the linearized representation is indicative of an appearance of a one-dimensional portion of the assay test strip.

8. The system of claim 1, wherein the at least one detector includes an array of detectors, and wherein the linearized representation is indicative of an appearance of a two-dimensional portion of the assay test strip.

9. The system of claim 2, wherein each optical detector respectively includes at least one optical element selected from the group consisting of aperture elements, lenses, mirrors, and diffractive elements.

10. The system of claim 1, wherein the assay test strip reader comprises at least one display device, and wherein the control electronics are further configured to cause output of an indication of the result on the display device.

11. The system of claim 1, wherein the assay test strip is associated with a biological test, and wherein the result is indicative of a result of the biological test.

12. The system of claim 11, wherein the result of the biological test includes a quantitative result.

13. The system of claim 11, wherein the result of the biological test includes a qualitative result.

14. The system of claim 11, wherein the control electronics enable a connection to a separate processor-based device such that the linearized representation of the assay test strip can be stored on a memory device of the separate processor-based device.

15. The system of claim 1, wherein the assay test strip is exposed to at least one biological fluid prior to insertion of the assay test strip in the body.

16. The system of claim 1, wherein the insertion of the assay test strip into the body causes the assay test strip reader to power-up.

17. A method of analyzing an assay test strip using the system of claim 1, said method comprising:
enabling an operator to move the assay test strip relative to the body of the assay test strip reader; and
detecting a presence of at least one analyte reaction region based on at least one characteristic of the at least one analyte reaction region during the operator-caused moving of the assay test strip relative to the body of the assay test strip reader.

18. The method of claim 17, further comprising outputting data indicative of the detected at least one characteristic of the at least one analyte reaction region using an audio/visual output device electrically connected to the at least one detector.

19. The method of claim 17, wherein the at least one characteristic includes at least one optical characteristic indicative of a presence of the at least one analyte reaction region.

20. The method of claim 19, further comprising illuminating at least a portion of the at least one analyte reaction region with at least one light source prior to detecting the at least one optical characteristic indicative of the presence of the at least one analyte reaction.

21. The method of claim 17, wherein enabling the operator to move the assay test strip relative to the body of the assay reader includes enabling the operator to insert the assay test strip in a test strip receiving area of the assay reader.

22. The method of claim 17, wherein the at least one detector includes at least one PIN-diode detector.

23. The method of claim 17, wherein the at least one detector includes at least one CMOS imager.

24. The method of claim 18, wherein outputting the data indicative of the detected at least one optical characteristic includes sending data to at least one processor-based device separate from the assay reader.

25. The method of claim 24, wherein the data is sent to the at least one processor-based device via a wired or a wireless connection selected from the group consisting of a WiFi connection, a Bluetooth connection and a USB connection.

26. The method of claim 17, wherein detecting the presence of the at least one analyte reaction region comprises generating the linearized representation of a one-dimensional portion of the assay test strip.

27. The method of claim 17, wherein the at least one detector includes a plurality of assay detectors fixedly connected to the body of the assay test strip reader in a linear arrangement perpendicular to a direction of motion of the assay test strip, and wherein detecting the presence of the at least one analyte reaction region comprises generating the linearized representation of a two-dimensional portion of the assay test strip.

28. The method of claim 17, wherein an insertion of the assay test strip into the body of the assay test strip reader causes the assay test strip reader to power-up.

* * * * *